United States Patent [19]

Yuan et al.

[11] Patent Number: 5,773,616

[45] Date of Patent: Jun. 30, 1998

[54] CERTAIN BRIDGED 4-PHENYL-2-AMINOMETHYLIMIDAZOLES; NEW DOPAMINE RECEPTOR SUBTYPE SPECIFIC LIGANDS

[75] Inventors: Jun Yuan, Clinton; Andrew Thurkauf, Danbury, both of Conn.

[73] Assignee: Neurogen Corporation, Branford, Conn.

[21] Appl. No.: 463,759

[22] Filed: Jun. 5, 1995

Related U.S. Application Data

[63] Continuation of Ser. No. 389,111, Feb. 15, 1995, abandoned.

[51] Int. Cl.⁶ .................... C07D 403/14; C07D 401/14
[52] U.S. Cl. .................... 544/295; 544/370; 544/319; 544/327; 544/328; 546/194; 546/256; 548/302.1
[58] Field of Search ................. 544/295, 370, 544/319, 327, 328; 546/194, 256; 548/302.1

[56] References Cited

U.S. PATENT DOCUMENTS

| | | | |
|---|---|---|---|
| 4,461,894 | 7/1984 | Omodei-Sale et al. | 544/370 |
| 5,214,040 | 5/1993 | Cuberes-Altisent et al. | 514/218 |
| 5,409,931 | 4/1995 | Caprathe et al. | 514/252 |
| 5,418,237 | 5/1995 | Bottcher et al. | 514/253 |
| 5,447,931 | 9/1995 | Baroni et al. | 514/252 |

*Primary Examiner*—Matthew V. Grumbling
*Attorney, Agent, or Firm*—McDonnell Boehnen Hulbert & Berghoff

[57] ABSTRACT

Disclosed are compounds encompassed by the following general formula:

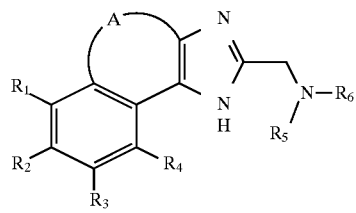

wherein,

A represents ethenylene, or A represents —X—CH$_2$—; where X is carbon or oxygen, provided that when X is oxygen, the oxygen is adjacent the 6-membered ring;

$R_1$, $R_2$, $R_3$ and $R_4$ are inorganic or organic substituents; and $R_5$ and $R_6$ is are optionally substituted organic substituents; or $NR_5R_6$ represents a carbocyclic or heterocyclic six membered ring optionally substituted with various orgainic or inorganic groups, which compounds can be used in the treatment of neuropsychological disorders.

8 Claims, No Drawings

CERTAIN BRIDGED 4-PHENYL-2-AMINOMETHYLIMIDAZOLES; NEW DOPAMINE RECEPTOR SUBTYPE SPECIFIC LIGANDS

This is a continuation application of U.S. Ser. No. 08/389,111, filed Feb. 15, 1995, now abandoned.

BACKGROUND OF THE INVENTION

1. Field of the Invention

This invention relates to certain bridged 4-phenyl-2-aminomethylimidazoles which selectively bind to dopamine receptor subtypes. This invention also relates to pharmaceutical compositions comprising such compounds. It further relates to the use of such compounds in the treatment of affective disorders such as schizophrenia, depression as well as certain movement disorders such as Parkinsonism and dystonia. Furthermore compounds of this invention are useful in treating the extrapyramidal side effects associated with the use of conventional neuroleptic agents.

2. Description of the Related Art

Schizophrenia or psychosis is a term used to describe a group of illnesses of unknown origin which affect approximately 2.5 million people in the United States. These disorders of the brain are characterized by a variety of symptoms which are classified as positive symptoms (disordered thought, hallucinations and delusions) and negative symptoms (social withdrawal and unresponsiveness). These disorders have an age of onset in adolescence or early adulthood and persist for many years. The disorders tend to become more severe during the patient's lifetime and can result in prolonged institutionalization. Within the United States of America, approximately 40% of all hospitalized psychiatric patients suffer from schizophrenia.

During the 1950's physicians demonstrated that they could successfully treat psychotic (schizophrenic) patients with medications called neuroleptics. This classification of antipsychotic medication was based largely on the activating (neuroleptic) properties of the nervous system by these drugs. Subsequently, neuroleptic agents were shown to increase the concentrations of dopamine metabolites in the brain. This finding suggested that altered neuronal firing of the dopamine system contributed in some way to the aberrant behavior observed in schizophrenic patients. Additional evidence indicated that dopamine could increase the activity of adenylate cyclase in the corpus striatum, an effect reversed by neuroleptic agents. Thus, cumulative evidence from these and later experiments strongly suggested that the neurotransmitter dopamine was involved in schizophrenia One of the major actions of antipsychotic medication is the blockade of dopamine receptors in brain. Several dopamine systems appear to exist in the brain and at least five classes of dopamine receptors appear to mediate the actions of this transmitter. These dopamine receptors differ in their pharmacological specificity and were originally classified on the basis of their ability to bind various dopaminergic ligands.

The butyrophenones are a class of drugs containing many potent antipsychotic drugs. Perhaps the most prominent member of this class of compounds is the antipsychotic drug haloperidol (1-(3-p-fluorobenzoylpropyl)-4-p-chlorophenyl-4-hydroxypiperidine). Haloperidol binds relatively weakly at the major dopamine receptor subtype which activates adenylate cyclase (commonly classified as the $D_1$ dopamine receptor). In contrast, haloperidol displayed binding affinity at a dopamine receptor subtype which suppressed the activity of adenylate cyclase (commonly classified as $D_2$ receptors) in the subnanomolar range.

Recently, three additional dopamine receptor subtypes have been identified using the often congruent sciences of receptor pharmacology and molecular biology. These new dopamine receptors have been labeled as $D_3$, $D_4$, and $D_5$. The $D_3$ and $D_4$ subtypes are pharmacologically related to the $D_2$ receptor via their ability to suppress the activity of adenylate cyclase. Conversely, the $D_5$ receptor is classified as a "$D_1$-like" dopamine subtype through its ability to stimulate cyclase activity.

Recently, a new group of drugs (such as sulpiride and clozapine) have been developed with a lesser incidence of extrapyramidal side effects (EPS) than classical neuroleptics. In addition, there is some indication that they may be more beneficial in treating negative symptoms in some patients. Since all $D_2$ blockers do not possess a similar profile, hypotheses underlying the differences have been investigated. Major differences have been detected in the anticholinergic actions of these drugs. It has also been suggested that the dopamine receptors in motor areas may differ from those in the limbic areas which are thought to mediate the antipsychotic responses. The existence of the $D_3$, $D_4$ and $D_5$ and other as yet undiscovered dopamine receptors may contribute to this profile. Some of the atypical compounds possess similar activity at $D_2$, $D_3$ and $D_4$ receptors. The examples of this patent fall into this general class of molecules.

Using molecular biological techniques it has been possible to clone cDNAs coding for each of the pharmacologically defined receptors. There are at least two forms of $D_1$ which have been identified as $D_1$ and $D_5$, and two forms of $D_2$, identified now as $D_2$ and $D_4$ dopamine receptors. In addition, there is at least one form of $D_3$ dopamine receptor.

International Publication No. WO 94/22839 describes certain 2-aminomethylbenzimidazoles as having affinity at dopamine receptors. The compounds of the present invention differ from those in WO 94/22839 in that the compounds of this invention possess a aromatic benzene ring fused in a [4,5-e] fashion to the benzimidazole substructure.

SUMMARY OF THE INVENTION

This invention provides novel compounds of Formula I which interact with dopamine receptor subtypes.

The invention provides pharmaceutical compositions comprising compounds of Formula I. The invention also provides compounds useful in treating affective disorders such as schizophrenia and depression as well as certain movement disorders such as Parkinsonism. Furthermore, compounds of this invention are useful in treating the extrapyramidal side effects associated with the use of conventional neuroleptic agents. Since particularly dopamine $D_3$ and $D_4$ receptor subtypes are concentrated in the limbic system (Science, 265: 1034 (Taubes, 1994)) which controls cognition and emotion, compounds which interact with these receptors are useful in the treatment of cognitive disorders. Such disorders include cognitive deficits which are a significant component of the negative symptoms (social withdrawal and unresponsiveness) of schizophrenia. Other disorders involving memory impairment or attention deficit disorders can also be treated with the compounds of this invention that interact specifically with dopamine $D_3$ and/or $D_4$ receptor subtypes. Accordingly, a broad embodiment of the invention is directed to compounds of Formula I:

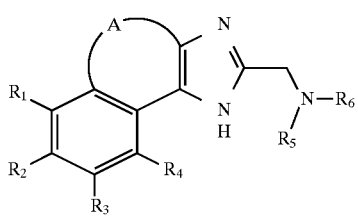

wherein
- A represents —CH=CH—, or A represents —X—CH$_2$—, where X is carbon or oxygen, provided that when X is oxygen, the oxygen is adjacent the 6-membered ring;
- $R_1$, $R_2$, $R_3$ and $R_4$ are the same or different and represent hydrogen, halogen, hydroxy, amino, aminosulfonyl, alkylaminosulfonyl, alkylsulfonyl, arylalkylsulfonyl, alkyl of 1 to 6 carbon atoms or alkoxy of 1 to 6 carbon atoms; and
- $R_5$ represents alkyl having 1–3 carbon atoms and $R_6$ is benzyl, optionally substituted with alkyl having 1–6 carbon atoms, alkoxy, hydroxy, or halogen; or
- $NR_5R_6$ represents heterocyclic six membered ring optionally substituted with alkyl having 1–6 carbon atoms, hydroxyl, halogen, aryl, alkylaryl where the alkyl portion is alkyl having 1–6 carbon atoms, or heteroaryl.

The invention also pertains to the use of compounds of general Formula I in the treatment of neuropsychological disorders. The pharmaceutical utility of compounds of this invention is indicated by the assays described below for dopamine receptor subtype affinity.

DETAILED DESCRIPTION OF THE INVENTION

In addition to compounds of general formula I described above, the present invention further encompasses compounds of Formula II:

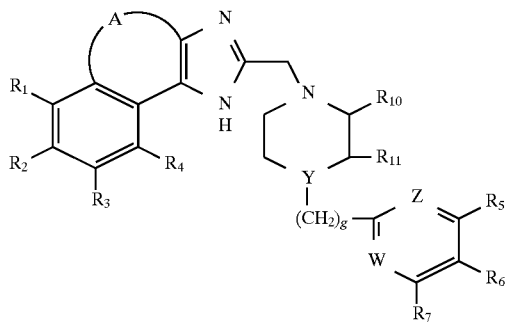

or the pharmaceutically acceptable salts thereof wherein:
- A represents —CH=CH—, or A represents —X—CH$_2$—; where X is carbon or oxygen, provided that when X is oxygen, the oxygen is adjacent the 6-membered ring;
- Y represents nitrogen or CH;
- W, Y and Z are the same or different and represent either carbon or nitrogen,
- $R_1$, $R_2$, $R_3$, $R_4$, $R_5$, $R_6$, and $R_7$ independently represent hydrogen, halogen, hydroxy, amino, aminosulfonyl, arylalkylsulfonyl or alkylsulfonyl where each alkyl portion has 1 to 6 carbon atoms, alkylaminosulfonyl where the alkyl portion has 1 to 6 carbon atoms, alkyl having 1 to 6 carbon atoms, or alkoxy of 1 to 6 carbon atoms;
- $R_{10}$ and $R_{11}$ are the same or different and represent alkyl groups having 1 to 6 carbon atoms;
- g is an integer from 0 to 4; and
- W and Z are both nitrogen; or
- W is $CR_8$ and Z is $CR_9$; or
- W is $CR_8$ and Z is nitrogen; or
- Z is $CR_9$ and W is nitrogen, where $R_8$ and $R_9$ are the same or different and represent hydrogen, halogen, alkyl having from 1 to 6 carbon atoms, or alkoxy having from 1 to 6 carbon atoms.

The invention also encompasses compounds of formula III:

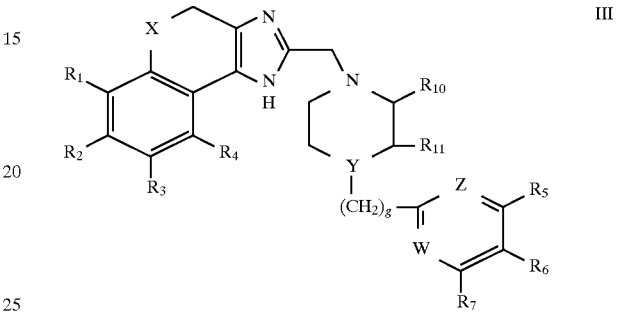

or the pharmaceutically acceptable salts thereof wherein:
- X is carbon or oxygen,
- Y represents nitrogen or CH;
- W, Y and Z are the same or different and represent either carbon or nitrogen,
- $R_1$, $R_2$, $R_3$, $R_4$, $R_5$, $R_6$, and $R_7$ independently represent hydrogen, halogen, hydroxy, amino, aminosulfonyl, arylalkylsulfonyl or alkylsulfonyl where the alkyl portion has 1 to 6 carbon atoms, alkylaminosulfonyl where each alkyl portion has 1 to 6 carbon atoms, alkyl having 1 to 6 carbon atoms, or alkoxy of 1 to 6 carbon atoms;
- $R_{10}$ and $R_{11}$ are the same or different and represent alkyl groups having 1 to 6 carbon atoms;
- g is an integer from 0 to 4; and
- W and Z are both nitrogen; or
- W is $CR_8$ and Z is $CR_9$; or
- W is $CR_8$ and Z is nitrogen; or
- Z is $CR_9$ and W is nitrogen, where $R_8$ and $R_9$ are the same or different and represent hydrogen, halogen, alkyl having from 1 to 6 carbon atoms, or alkoxy having from 1 to 6 carbon atoms.

The invention further encompasses compounds of formula IV:

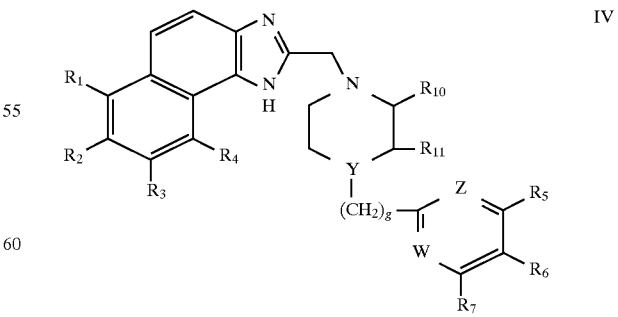

or the pharmaceutically acceptable salts thereof wherein
- Y represents nitrogen or CH;
- W, Y and Z are the same or different and represent either carbon or nitrogen, $R_1$, $R_2$, $R_3$, $R_4$, $R_5$, $R_6$, and $R_7$ independently represent hydrogen, halogen, hydroxy, amino, aminosulfonyl, arylalkylsulfonyl or alkylsulfonyl where each alkyl portion has 1 to 6 carbon atoms, alkylaminosulfonyl where the alkyl portion has 1 to 6 carbon atoms, alkyl having 1 to 6 carbon atoms, or alkoxy of 1 to 6 carbon atoms;

$R_{10}$ and $R_{11}$ are the same or different and represent alkyl groups having 1 to 6 carbon atoms;

g is an integer from 0 to 4; and

W and Z are both nitrogen; or
W is $CR_8$ and Z is $CR_9$; or
W is $CR_8$ and Z is nitrogen; or
Z is $CR_9$ and W is nitrogen, where $R_8$ and $R_9$ are the same or different and represent hydrogen, halogen, alkyl having from 1 to 6 carbon atoms, or alkoxy having from 1 to 6 carbon atoms.

The invention also provides compounds of formula V:

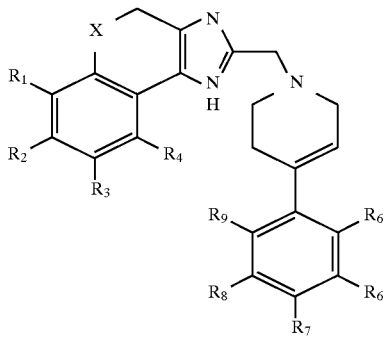

wherein,

X is carbon or oxygen; and $R_1$, $R_2$, $R_3$, $R_4$, $R_5$, $R_6$, $R_7$, $R_8$ and $R_9$ are the same or different and represent hydrogen, halogen, hydroxy, amino, aminosulfonyl, arylalkylsulfonyl, alkylsulfonyl, alkylaminosulfonyl, alkyl of 1 to 6 carbon atoms or alkoxy of 1 to 6 carbon atoms.

The invention also provides compounds of formula VI:

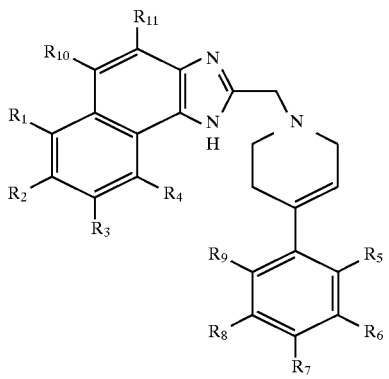

wherein, $R_1$, $R_2$, $R_3$, $R_4$, $R_5$, $R_6$, $R_7$, $R_8$, $R_9$, $R_{10}$ and $R_{11}$ are the same or different and represent hydrogen, halogen, hydroxy, amino, aminosulfonyl, arylalkylsulfonyl, alkylsulfonyl, alkylaminosulfonyl, alkyl of 1 to 6 carbon atoms or alkoxy of 1 to 6 carbon atoms.

The invention also provides compounds of formula VII:

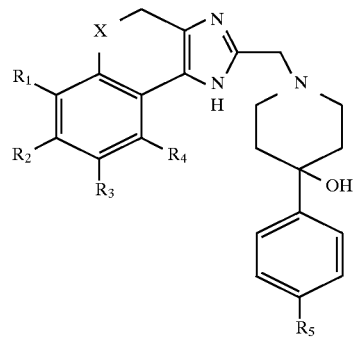

wherein

X is carbon or oxygen; and $R_1$, $R_2$, $R_3$, $R_4$ and $R_5$ are the same or different and represnt hydrogen, halogen, hydroxy, amino, aminosulfonyl, arylalkylsulfonyl, alkylsulfonyl, alkylaminosulfonyl, alkyl of 1 to 6 carbon atoms or alkoxy of one to six carbon atoms.

The invention also provides compounds of formula VIII:

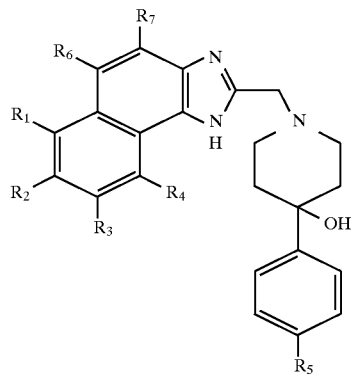

wherein

X is carbon or oxygen; and $R_1$, $R_2$, $R_3$, $R_4$, $R_5$, $R_6$ and $R_7$ are the same or different and represent hydrogen, halogen, hydroxy, amino, aminosulfonyl, arylalkylsulfonyl, alkylsulfonyl, alkylaminosulfonyl, alkyl of 1 to 6 carbon atoms or alkoxy of 1 to 6 carbon atoms.

The invention also provides compounds of formula IX:

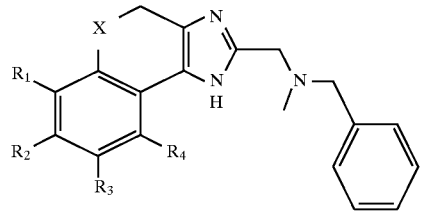

wherein

X is carbon or oxygen; and $R_1$, $R_2$, $R_3$, and $R_4$ are the same or different and represent hydrogen, halogen, hydroxy, amino, aminosulfonyl, arylalkylsulfonyl, alkylsulfonyl, alkylaminosulfonyl, alkyl of 1 to 6 carbon atoms or alkoxy of 1 to 6 carbon atoms.

The invention also provides compounds of formula X:

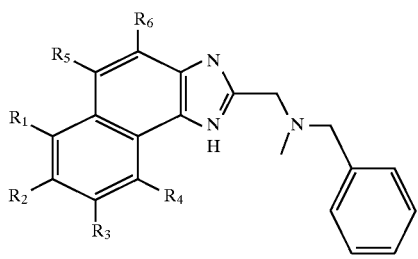

wherein $R_1$, $R_2$, $R_3$, $R_4$, $R_5$, and $R_6$ are the same or different and represent hydrogen, halogen, hydroxy, amino, aminosulfonyl, arylalkylsulfonyl, alkylsulfonyl, alkylaminosulfonyl, alkyl of 1 to 6 carbon atoms or alkoxy of 1 to 6 carbon atoms.

Preferred "$NR_5R_6$" groups of formula I above include the following:

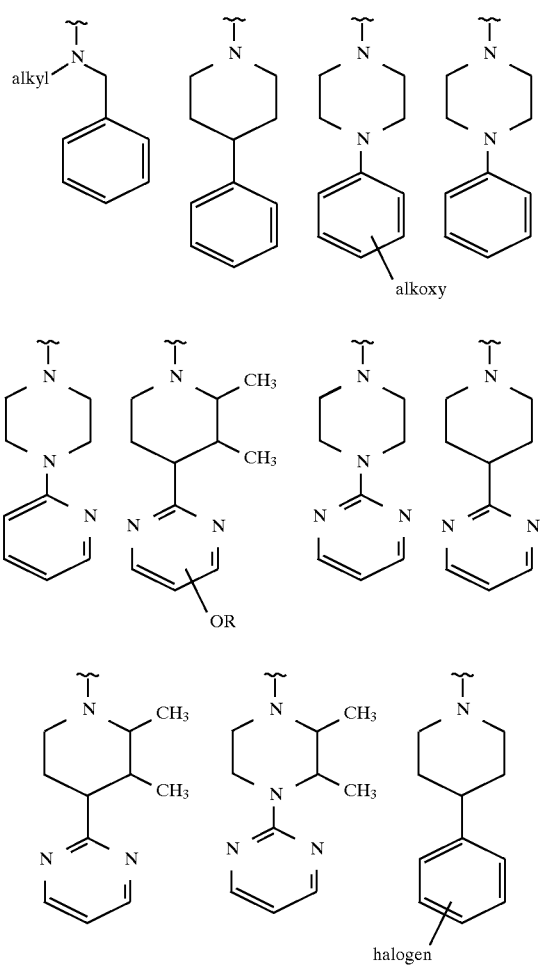

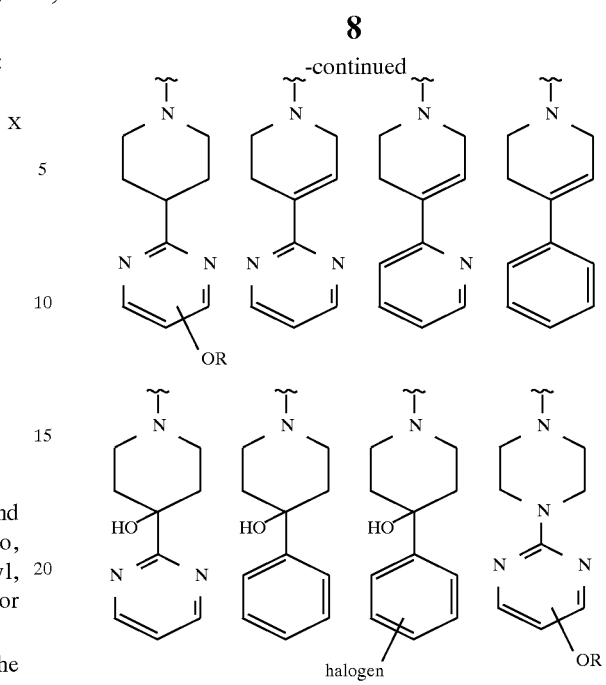

In the above preferred $NR_5R_6$ groups, OR represents hydroxy or alkoxy.

Particularly preferred $NR_5R_6$ substituents are N-benzyl-N-methyl, 4-(2-pyrimidinyl)piperazinyl, and 4-phenylpiperidinyl groups.

Representative compounds of the present invention, which are encompassed by Formula I, include, but are not limited to the compounds in FIG. 1 and their pharmaceutically acceptable salts. Non-toxic pharmaceutically acceptable salts include salts of acids such as hydrochloric, phosphoric, hydrobromic, sulfuric, sulfinic, formic, toluene sulfonic, hydroiodic, acetic and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which can be employed to prepare non-toxic pharmaceutically acceptable addition salts and acylated prodrugs of the compounds encompassed by Formula I.

When A represents —CH=CH— in the formulas set forth above, the resulting unsaturated system is a 1H-naphth[1,2-d]imidazole.

By "aryl" and "Ar" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which can optionally be unsubstituted or substituted with e.g., halogen, lower alkyl, lower alkoxy, lower alkylthio, trifluoromethyl, lower acyloxy, aryl, heteroaryl, and hydroxy.

By "alkyl" and "lower alkyl" is meant straight and branched chain alkyl groups having from 1–6 carbon atoms.

By "lower alkoxy" and "alkoxy" is meant straight and branched chain alkoxy groups having from 1–6 carbon atoms.

By "heteroaryl" is meant 5, 6, or 7 membered aromatic ring systems having at least one hetero atom selected from the group consisting of nitrogen, oxygen and sulfur.

Examples of heteroaryl groups are pyridyl, pyrimidinyl, pyrrolyl, pyrazolyl, pyrazinyl, pyridazinyl, oxazolyl, furanyl, quinolinyl, isoquinolinyl, thiazolyl, and thienyl, which can optionally be unsubstituted or substituted with e.g., halogen, lower alkyl, lower alkoxy, lower alkylthio, trifluoromethyl, lower acyloxy, aryl, heteroaryl, and hydroxy.

By halogen is meant fluorine, chlorine, bromine and iodine.

By alkylsulfonyl is meant a sulfonyl group substituted with a lower alkyl group.

By arylalkylsulfonyl is meant a sulfonyl group substituted with an arylalkyl group.

By aminosulfonyl is meant a sulfonyl group substituted with an amino group.

By alkylaminosulfonyl is meant a sulfonyl group substituted with a lower alkylamino, or di-lower alkylamino group.

Representative examples of bridged 4-phenyl-2-aminomethylimidazoles according to the invention are shown in Table I below.

TABLE 1[1]

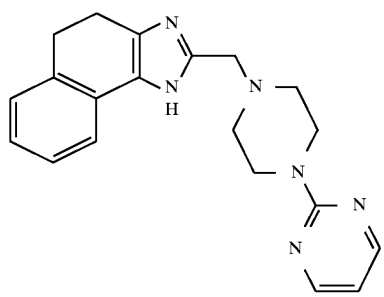

1

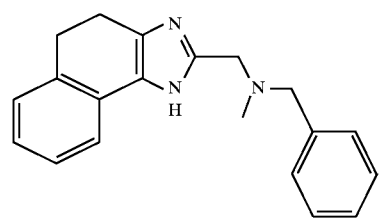

2

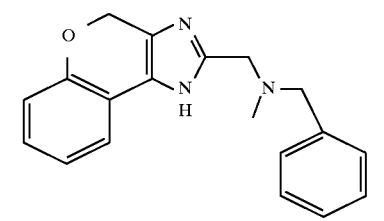

3

TABLE 1[1]-continued

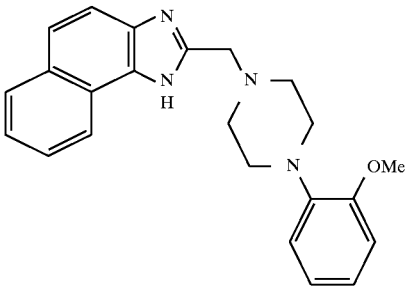

4

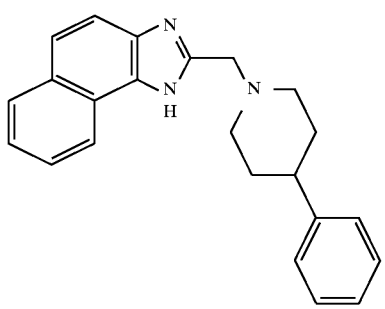

5

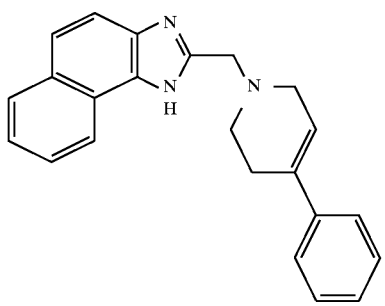

6

[1]The number below each compound is its compound number.

The pharmaceutical utility of compounds of this invention are indicated by the following assays for dopamine receptor subtype affinity which demonstrate the interaction of the compounds with dopamine receptor subtypes. The interaction results in the pharmacological activities of these compounds which thus can be exploited in the treatment of affective disorders such as schizophrenia, depression as well as certain movement disorders such as Parkinsonism and dystonia. Furthermore, compounds of this invention are useful in treating the extrapyramidal side effects associated with the use of conventional neuroleptic agents.

Assay for $D_2$ and $D_3$ Receptor Binding Activity

Pellets of COS cells containing recombinantly produced $D_2$ or $D_3$ receptors from African Green monkey were used for the assays. The sample is homogenized in 100 volumes (w/vol) of 0.05M Tris HCl buffer at 4° C. and pH 7.4. The sample is then centrifuged at 30,000×g and resuspended and rehomogenized. The sample is then centrifuged as described and the final tissue sample is frozen until use. The tissue is resuspended 1:20 (wt/vol) in 0.05M Tris HCl buffer containing 100 mM NaCl.

Incubations are carried out at 48° C. and contain 0.4 ml of tissue sample, 0.5 nM $^3$H-YM 09151-2 and the compound of interest in a total incubation of 1.0 ml. Nonspecific binding is defined as that binding found in the presence of 1 $\mu$M spiperone; without further additions, nonspecific binding is less than 20% of total binding. The binding characteristics of examples of this invention for the $D_2$ and $D_3$ receptor subtypes are shown in Table 2 for Rat Striatal Homogenates.

TABLE 2

| Compound Number[1] | $D_2$ $K_i$ ($\mu$M) | D3 $K_i$ ($\mu$M) |
|---|---|---|
| 1 | 4.200 | 7.800 |
| 2 | 0.350 | 0.210 |
| 3 | 0.220 | 0.440 |

[1]Compound numbers relate to compounds shown in Table 1.

Assay for $D_4$ Receptor Binding Activity

Clonal cell lines expressing the human dopamine $D_4$ receptor subtype were harvested in PBS and the cells centrifuged and the pellets stored at −80° C. until used in the binding assay. The pellets were resuspended and the cells lysed at 4° C. in 50 mM Tris pH 7.4 buffer containing 120 mM NaCl, 1 mM EDTA and 5 mM $MgCl_2$. The homogenate is centrifuged at 48000×g for 10 minutes at 4° C. The resulting pellet is resuspended in fresh buffer and centrifuged again. After resuspension of the pellet in fresh buffer a 100 ml aliquot is removed for protein determination. The remaining homogenate is centrifuged as above, the supernatant removed and the pellet stored at 4° C. until needed at which time it is resuspended to a final concentration of 625 mg/ml (250 mg per sample) with 50 mM Tris buffer (pH 7.4) and 120 mM NaCl just prior to use. Incubations were carried out for 60 minutes at 25° C. in the presence of 0.1 nM [$^3$H] YM-09151-2. The incubation was terminated by rapid filtration through Whatman GF/C filters and rinsed with 2×4 ml washes of chilled 50 mM Tris (pH 7.4) and 120 mM NaCl. Non-specific binding was determined with 1 $\mu$M spiperone and radioactivity determined by counting in an LKB beta counter. Binding parameters were determined by non-linear least squares regression analysis, from which the inhibition constant Ki could be calculated for each test compound. The binding characteristics of some examples of this invention are shown in Table 3 for the dopamine $D_4$ binding assay. In general, compounds of the accompanying Examples were tested in the above assay, and all were found to possess a Ki value for the displacement of [$^3$H]YM-09151-2 from the human dopamine $D_4$ receptor subtype of below 500 nM. Some specific data is indicated in Table 3.

TABLE 3

| Compound Number[1] | $K_i$ ($\mu$M) |
|---|---|
| 1 | 0.012 |
| 2 | 0.081 |
| 3 | 0.145 |

[1]Compound numbers relate to compounds shown in Table 1.

Compounds 1 and 2 are particularly preferred embodiments of the present invention because of its potency in binding to dopamine receptor subtypes.

The compounds of the invention, or a pharmaceutically acceptable salt thereof, i.e., the "active ingredient", can be used alone or in combination with various excipients, stabilizers or agents to designed to prolong the action of the active ingredient in the treatment of neuropsychochological disorders such as, example, schizophrenia, dementia, depression, anxiety, Parkinson-like motor disorders and motion disorders related to the use of neuroleptic agents.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitor or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Representative procedures suitable for the preparation of compounds of the present invention are illustrated in Schemes 1 and 2. Those having skill in the art will recognize that the starting materials may be varied and additional steps employed to produce compounds encompassed by the present invention.

Scheme 1 depicts a representative route for the preparation of ethyl and oxomethyl bridged 4phenyl-2-aminomethylimidazoles of the invention.

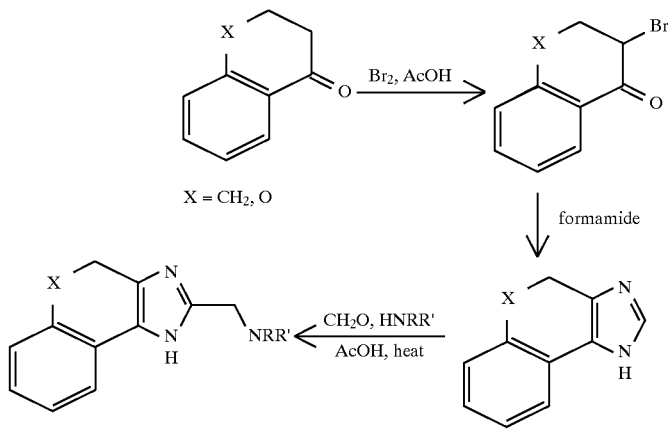

Scheme 1

Scheme 2 shows a representative route for the preparation of the ethylene bridged 4-phenyl-2-aminomethylimidazoles of the invention.

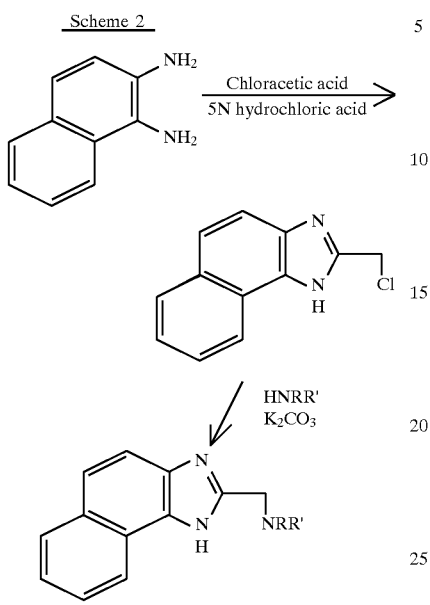

In each of Schemes 1 and 2 above, NRR' represents the group $NR_5R_6$ defined above or a protected precursor thereof.

This invention is further illustrated by the following examples which are not to be construed as limiting the invention in scope or spirit to the specific procedures and compounds described therein.

Example 1

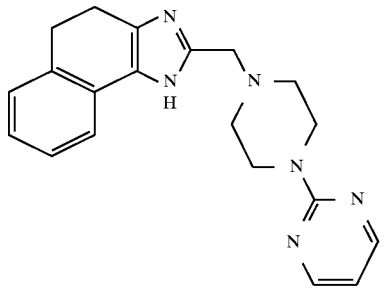

1. A solution of bromine (5.5 g) in 25 ml of acetic acid was added dropwise to a solution of 1-tetralone in 25 ml of acetic acid at 60° C. After the addition was complete, the reaction was cooled and most of the acetic acid was removed in vacuo. The residue was partitioned between water and ethyl acetate. The organic layer was washed with a dilute solution of sodium bisulfite, dried with sodium sulfate and concentrated. A portion of the resulting 2-bromo-1-tetralone (3 g) was mixed with 30 ml of formamide and the resulting solution was heated at 160° C. for 12 hours. Upon cooling, 100 ml of water was added followed by 10 ml of 3N hydrochloric acid solution. The mixture was washed with diethyl ether and the ether layer was discarded. The remaining solution was made basic with saturated sodium carbonate solution and extracted with methylene chloride. The organic extracts were dried with sodium sulfate and concentrated to provide 1.2 g of 4,5-dihydronaphth[1,2-d]imidazole.

2. A solution of 100 mg of 4,5-dihydronaphth[1,2-d]imidazole, 51 mg of 37% w/w aqueous formaldehyde, 103 mg of 1-(2-pyrimidinyl)piperazine in 5 ml of acetic acid was refluxed for 1 hour, cooled and the solvent removed under reduced pressure. Ethanol (3 ml) and ammonium hydroxide (0.1 ml) were added and the solution was reconcentrated. Purification of the product on silica gel using 10% v/v methanol/chloroform as the eluent provided 1H-2-(1-(4-(2-pyrimidyl)piperazinyl))methyl-(5,6-dihydro)-naphth[1,2-d]-imidazole as an oil. The addition of a saturated solution of hydrogen chloride in isopropanol to the product in isopropanol yielded the amine salt which was isolated by filtration to provide 151 mg of: 1H-2-(1-(4-(2-pyrimidyl)piperazinyl))methyl-(5,6-dihydro)-naphth[1,2-d]imidazole dihydrochloride (Compound 1, m.p. 212°–214° C.).

EXAMPLE 2

The following compounds are prepared essentially according to the procedure described in Example 1.
(a) 1H-{2-(N-benzyl-N-methyl)aminomethyl}-(5,6-dihydro)-naphth[1,2-d]imidazole dihydrochloride (Compounds 2, m.p. 225°–227° C.).
(b) 1H-{2-(N-benzyl-N-methyl)aminomethyl}chromano[3,4-d]imidazole dihydrochloride (Compound 3, m.p. 198°–201° C. dec.).

EXAMPLE 3

Monochloroacetic acid (15 g, 0.16 mol) and diaminonaphthlene (22.1 g, 0.14 mol) were refluxed in 60 ml of 5N HCl for 6 hours. The reaction was cooled in ice and neutralized with aqueous ammonium hydroxide. The precipitated product was collected by filtration and recrystallized from benzene/hexane (18.7 g, 62%).

To a solution of the isolated 2-chloromethyl-1H-naphth[1,2-d]imidazole (1.4 g, 6.5 mmol) in dimethylformamide (20 ml) was added potassium carbonate (2 g) and the resultant mixture was refluxed for 2 hours. After cooling to 20° C., the reaction mixture was poured onto ice water and extracted with chloroform. The organic extracts were dried and concentrated to give an oil. The oil was dissolved in 10 ml of isopropyl alcohol and 48% HBr was added dropwise until the pH of the solution was less than 3.0 as indicated by pH paper. A precipitate developed upon standing which was isolated by filtration providing 1H-2-(1[4-(2-methoxyphenyl)piperazinyl]]methylnaphth[1,2-d]imidazole dihydrobromide (Compound 4, 2.7 g, 77%).

EXAMPLE 4

The following compounds are prepared essentially according to the procedure described in Example 3.
(a) 2-[1-(4-phenyl)piperidinyl]methyl-1H-naphth[1,2-d]imidazole dihydrochloride (Compound 5).
(b) 2-[1-{4-phenyl-1,2,3,6-tetrahydro}pyridyl]methyl-1H-naphth[1,2-d]imidazole dihydrochloride (Compound 6).
(c) 2-[1-{4-hydroxy-4-(4-chlorophenyl)}piperidinyl]methyl-1H-naphth[1,2-d]imidazole dihydrochloride (Compound 7).

The invention and the manner and process of making and using it are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude the specification.

What is claimed is:

1. A compound of the formula:

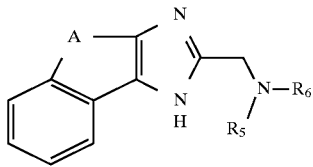

or the pharmaceutically acceptable salts thereof wherein:

A represents —CH=CH—, or A represents —X—CH$_2$—, where X is methylene or oxygen, provided that when X is oxygen, the oxygen is adjacent the 6-membered ring; and NR$_5$R$_6$ represents
  piperazinyl substituted in the 4-position with 2-pyrimidinyl or optionally substituted phenyl;
  piperidinyl substituted in the 4-position with 2-pyrimidinyl or optionally substituted phenyl; or
  1, 2, 3, 6-tetrahydropyridyl substituted in the 4-position with 2-pyrimidinyl or optionally substituted phenyl.

2. A compound according to claim 1, where A is methylene.

3. A compound according to claim 1 where A is —OCH$_2$—, where the oxygen is adjacent to the 6-membered ring.

4. A compound according to claim 1, wherein NR$_5$R$_6$ represents 4-phenyl-1,2,3,6-tetrahydropyridyl.

5. A compound according to claim 1, wherein NR$_5$R$_6$ represents 4-phenyl-piperidinyl.

6. A compound according to claim 1, wherein NR$_5$R$_6$ represents 4-(2-pyrimidyl)piperazinyl.

7. A compound according to claim 1, wherein NR$_5$R$_6$ represents 4-(2-methoxyphenyl)piperazinyl.

8. A compound according to claim 1, wherein NR$_5$R$_6$ represents 4-hydroxy-4-(4-chlorophenyl)piperidinyl.

* * * * *